US00PP28358P3

(12) United States Plant Patent
Mazzardis

(10) Patent No.: US PP28,358 P3
(45) Date of Patent: Sep. 5, 2017

(54) BLUEBERRY PLANT NAMED 'EB 9-12'

(50) Latin Name: ***Vaccinium* Hybrid**
Varietal Denomination: EB 9-12

(71) Applicant: Vincent David Mazzardis, Joondalup (AU)

(72) Inventor: Vincent David Mazzardis, Joondalup (AU)

(73) Assignee: Bisa Trading Pty. Ltd., Cannington (AU)

( * ) Notice: Subject to any disclaimer, the term of this patent is extended or adjusted under 35 U.S.C. 154(b) by 19 days.

(21) Appl. No.: 14/756,636

(22) Filed: Sep. 28, 2015

(65) Prior Publication Data

US 2016/0113168 P1 Apr. 21, 2016

(30) Foreign Application Priority Data

Oct. 16, 2014 (AU) ..... 2014/245

(51) Int. Cl.
*A01H 5/08* (2006.01)

(52) U.S. Cl.
USPC ..... Plt./157

(58) Field of Classification Search
USPC ..... Plt./157
See application file for complete search history.

(56) References Cited

FOREIGN PATENT DOCUMENTS

AU 2014/24 10/2014

OTHER PUBLICATIONS

Plant Varieties Journal, vol. 28, No. 1: published Jun. 15, 2015.

*Primary Examiner* — Susan McCormick Ewoldt
(74) *Attorney, Agent, or Firm* — Randall Danskin P.S.

(57) ABSTRACT

A new and distinct variety of blueberry plant, which is denominated varietally as 'EB 9-12' is described, and which produces large to very large sized fruit, and which further has a very good fruit flavor, and an earlier flowering, and fruit production date when grown under the ecological conditions prevailing in Yanchep Springs, Western Australia.

1 Drawing Sheet

Latin name: '*Vaccinium* Hybrid'.
Varietal denomination: 'EB 9-12'.

RELATED APPLICATION DATA

The present application claims priority to Australian Plant Breeders Rights Application, Serial No. 2014/245, and which was filed on Oct. 16, 2014, and accepted on Dec. 23, 2014.

BACKGROUND OF THE NEW VARIETY

The present invention relates to a new, novel, and distinct variety of blueberry plant '*Vaccinium* hybrid' and which has been denominated varietally as 'EB 9-12'.

ORIGIN AND ASEXUAL REPRODUCTION OF A NEW VARIETY

The present variety of blueberry plant resulted from an ongoing development program of plant breeding. The purpose of this program is to improve the commercial quality of various plant varieties by creating and releasing promising selections of plants including blueberries. To this end, I have made both controlled and hybrid cross-pollinations each year in order to produce resulting plant populations from which improved progenies are evaluated and selected.

The blueberry plant 'EB 9-12' was derived from a cross-pollination employing the blueberry plant 'BB-2' [unpatented], and the pollen parent '03-6' [unpatented] during the 2006 growing season. This first controlled cross pollination took place at Yanchep Springs, Yanchep, Western Australia. The seed parent 'BB-2' is characterized by an upright bush-type growth habit; a mid- to late season flowering date; and which further produces large, firm fruit. On the other hand, the pollen parent '03-6' [unpatented] is characterized by a spreading growth habit, an earlier flowering date, and which further produces fruit having a large size. Seed from the seed parent 'BB-2' produced approximately 500 plants. These plants were then grown, and the first fruit was evaluated during the 2008 growing season. Further, an additional assessment of these same plants took place in 2009. At that time the new variety 'EB 9-12' was then selected for further asexual reproduction, and evaluation. The present variety was asexually reproduced by cuttings, and the plants produced from this first asexual propagation were later evaluated during the 2010 through 2014 growing seasons. The subsequent evaluations of these asexually reproduced plants show that they were true to the original plant, and it was my conclusion following those evaluations that 'EB 9-12' was a new, novel and distinct variety of blueberry plant. The asexual reproduction of Blueberry Plant EB 9-12 occurred at Yanchep Springs, Yanchep Western Australia.

The new, present variety of blueberry plant is characterized as to novelty by displaying a semi-upright bush-type growth habit; and which further produces large to very large and slightly flat fruit which have an excellent flavor, a very early flowering date, and an early fruit maturity date. The most closely known plant varieties which relate to the present new plant concerns the blueberry plant 'Ridley 1111' which is further identified as U.S. Plant Pat. No. 23,572 and which was filed on Jan. 18, 2011; and blueberry plant 'EB 8-46' which is further identified as U.S. Plant Pat. No. 26,173, and which was filed on Nov. 21, 2013). With regard to the 'Ridley 1111' blueberry plant, the new variety of blueberry plant produces fruit which are considered large to very large in size, in relative comparison to the fruit produced by the 'Ridley 1111' blueberry plant, and which produces only medium to large fruit. On the other hand, and with regard to the blueberry plant 'EB 8-46', the new, present variety of blueberry plant is distinguishable therefrom by displaying a strong, to very strong plant vigor; an upright to semi-upright growth habit; a lanceolate leaf shape; a medium green, unripe fruit color; and a fruit weight which is less than that expressed by the variety 'EB 8-46'. These distinguishing features of the closest known variety 'EB 8-46' as well as the distinctions relative to the parent plants 'BB-2' [unpatented]; and '03-6' [unpatented] will be discussed in the paragraphs which follow.

BRIEF DESCRIPTION OF THE DRAWINGS

The accompanying drawing is a color photograph of the new blueberry plant, at an age of two (2) years, in juxtaposition relative to an image of the closest known variety 'EB 8-46' (U.S. Plant Pat. No. 26,173). The photograph depicts several mature fruit of the new variety which is sufficiently matured for harvesting and shipment. The photograph also depicts a typical vegetative stem bearing typical leaves and at least one leaf showing the ventral coloration thereof, as well as two mature fruit of the present new variety. Similar plant features are seen in the image which relates to the closest known variety 'EB 8-46'. The colors in this photograph are as nearly true as is reasonably possible on a color representation of this type. Due to chemical development, processing and printing, the leaves and fruit depicted in these photographs may or may not be accurate when compared to the actual specimen. For this reason, future color references should be made to the descriptions as provided hereinafter.

NOT A COMMERCIAL WARRANTY

The following detailed description has been prepared to solely comply with the provisions of 35 U.S.C. §112, and does not constitute a commercial warranty, (either expressed or implied), that the present variety will, in the future, display the botanical, horticultural, or other characteristics as set forth, hereinafter. Therefore, this disclosure may not be relied upon to support any future legal claims including, but not limited to, breach of warranty of merchantability, or fitness for any particular purpose, or non-infringement, which is directed, in whole, or in part, to the present variety.

DETAILED DESCRIPTION

Referring more specifically to the botanical details of this new and distinct variety of blueberry plant, the following has been observed during the sixth fruiting season under the ecological conditions prevailing at the farm of the inventor, and which is located near Yanchep Springs, Western Australia.

The colors and codes used herein to describe the EB 9-12 plant, refer to The Royal Horticultural Society (R.H.S.) Colour Chart, 5$^{th}$ Ed., 2007.

The age of the plant at the time of the description that follows herein is three (3) years.

Plant:

*Plant vigor*.—The present variety of blueberry plant is considered to have a strong to very strong plant vigor. This is in contrast to the closest known variety 'EB 8-46' and where the plant vigor characteristic which is displayed is only considered average to strong.

*Plant growth habit*.—Considered upright to semi-upright. This is in contrast to the closest known variety 'EB 8-46' and where the plant growth habit is only considered average. In contrast to the seed parent 'BB 2' [unpatented], the plant growth habit of this parent plant is upright and bush-type. On the other hand, the pollen parent '03-6' displays a spreading growth habit.

*One year old shoots*.—Yellow Green 150C (R.H.S. Colour Chart, 5$^{th\ Ed.}$ 2007).

*Internode length*.—Considered long for the species, about 13.6 mm. This is in contrast to the closest known variety 'EB 8-46', (U.S. Plant Pat. No. 26,173) and where this same growth characteristic is only considered average. Height of plant at time of description herein is about 1.5 m. Width of plant at time of description is about 1 m.

*Bark color is*.—Greyed Orange, 176B (R.H.S. Colour Chart, 5$^{th}$ Ed., 2007).

*Leaf length*.—Considered very long for the species, about 65.80 mm., on average. This is in contrast to the closest known variety 'EB 8-46' where the average leaf length is about 60.33 mm.

*Leaf width*.—Considered narrow for the species, about 29.93 mm. This is in contrast to the closest known variety 'EB 8-46', and where the average leaf width is about 34.1 mm.

*Leaf ratio*.—Length/Width — Considered large to very large for the species. This is in contrast to the same growth characteristic as expressed in the closest known variety 'EB 8-46' and which is considered merely average.

*Leaf shape*.—Generally Elliptic. This is in contrast to the closest known variety 'EB 8-46' (U.S. Plant Pat. No. 26,173), and where the leaf shape is considered ovate.

*Leave color*.—Dorsal Surface — Yellow Green 147A (R.H.S. Colour Chart, 5$^{th}$ Ed., 2007).

*Leaf color*.—Under Surface is — Yellow Green 148B (R.H.S. Colour Chart, 5$^{th}$ Ed. 2007).

*Texture of leaf is*.—Glabrous.

*Leaf apex shape is*.—Acute.

*Leaf apex base shape is*.—Acute.

*Vein color of the leaf is*.—Yellow Green 144C (R.H.S. Colour Chart, 5$^{th}$ Ed., 2007).

*Venation pattern of the leaf is*.—Pinnately reticulate.

*Leaf arrangement is*.—Alternate.

*Color intensity*.—Dorsal Surface — In relative comparison to the leaf color as expressed in the closest known variety 'EB 8-46', the dorsal leaf color of the present variety is only considered average, as compared to the medium to dark green color as seen in the leaves produced by the blueberry plant 'EB 8-46'.

*Seed color*.—Greyed Orange N172B (R.H.S. Colour Chart, 5th Ed., 2007).

*Leaf marginal edge*.—Generally — Considered entire.

Flowers:

*Flower bud coloration*.—The anthocyanin coloration is considered to be very weak.

*Inflorescence length*.—Considered average for the species, about 25 mm.

*Color of opened flower is*.—White 155C (R.H.S. Colour Chart, 5th Ed., 2007).

*Average number of flowers per inflorescence is*.—10.

*Corolla texture is*.—Rigid.

*Corolla length is*.—About 10.5 mm.

*Corolla diameter is*.—About 11 mm.

*Corolla color is*.—White NN155C (R.H.S. Colour Chart, 5th Ed., 2007).

*Corolla aperture size is*.—About 4 mm.

*Pedicle length is*.—About 5.5 mm.

*Pedicle color is*.—Green 142C (R.H.S. Colour Chart, 5th Ed., 2007).

*Corolla shape*.—Urceolate.

*Corolla tube*.—Size — Considered average for the species.

*Corolla tube coloration*.—Generally speaking any anthocyanin coloration of the corolla tube is considered absent or very weak.

*Corolla tube ridges*.—Present.

Fruit:

*Fruit cluster density*.—Generally considered medium to dense for the species.

*Unripe fruit color*.—Yellow Green 150C (R.H.S. Colour Chart, 5th Ed., 2007). This is in contrast to the coloration as expressed on the unripe fruit of the closest known variety 'EB 8-46' (U.S. Plant Pat. No. 26,173), and where this coloration is considered an average green.

*Fruit size*.—Considered large to very large for the species. In this regard, the average fruit diameter is about 17.92 mm.; and the average fruit height is about 13.92 mm. This is in contrast to the closest known variety 'EB 8-46', and where the average fruit diameter is about 19.57 mm.; and the average fruit height is about 14.34 mm.

*Fruit shape when viewed in a longitudinal section*.—Considered oblate.

*Sepal position/attitude*.—The new variety is considered to be erect to semi-erect.

*Sepal type*.—Generally — Incurving.

*Calyx basin diameter*.—Considered small to medium. In this regard, the Calyx basin diameter (width) is about 7.40 mm.; and the Calyx basin depth is about 2.08 mm. This is in contrast to the closest known variety 'EB 8-46', and where the Calyx basin width is about 8.22 mm., and the Calyx basin depth is about 3.38 mm.

*Fruit*.—Intensity of Fruit Bloom — Considered strong to very strong.

*Fruit skin color*.—Black 203C (R.H.S. Colour Chart, 5th Ed., 2007). Fruit flesh color (Ripened Fruit) is Greyed Green 189D (R.H.S. Colour Chart, 5th Ed. 2007).

*Fruit*.—Firmness — Considered firm to very firm.

*Fruit weight*.—Generally speaking about 2.85 gm., on average. This is in contrast to the average weight of the fruit produced by the closest known variety 'EB 8-46', and which weighs about 3.76 gm.

*Fruiting type*.—Generally speaking fruiting occurs on one-year old and current season's shoots.

*Vegetative bud burst*.—Not applicable as the Blueberry plant EB 9-12 is an Evergreen.

*Beginning of flowering on current year's shoots*.—June-July, this is considered to occur early in the season for the specified location of culture.

*Duration of bloom time*.—6-8 weeks.

*Fruit sweetness*.—Considered high to very high for the species.

*Resistance to insects and diseases*.—No particular susceptibilities were noted. The present blueberry variety has not been tested to expose or detect any susceptibilities or resistances to any known plant and/or fruit diseases.

Reproductive organs of the plant:

*Size of the pollen anthers is*.—About 8.7 mm.

*Color of the pollen anthers is*.—Greyed Orange 165B (R.H.S. Colour Chart, 5th Ed., 2007).

*Pistil length is*.—About 10.3 mm.

*Pistil color is*.—Yellow Green 145B (R.H.S. Colour Chart, 5th Ed., 2007). Market use of the fruit is First Grade Fresh Market Fruit.

*Pollination requirement is*.—Self-fertile.

Fruit productivity:

*Average weight of fruit is*.—About 2.85 g. Storability of the plant fruit is considered to be long. The observed date of the first pick is approximately September in the specified location of culture. The observed date of the last pick is approximately December in the specified location of culture. Although the new variety of blueberry plant possesses the described characteristics when grown under the ecological conditions prevailing near Yanchep Springs, Western Australia, it should be understood that the variations of the usual magnitude and characteristics incident to changes in growing conditions, fertilization, pruning, pest control, frost, climatic variables and horticultural management are to be expected.

Having thus described and illustrated my new variety of blueberry plant, what I claim is new, and desire to secure by plant Letters Patent is:

1. A new and distinct variety of blueberry plant substantially as illustrated and described, and which is characterized principally as to novelty by producing a large to very large fruit which has a good flavor, and an earlier flowering and fruit production dates, when grown under the ecological conditions prevailing near Yanchep Springs, Western Australia.

* * * * *

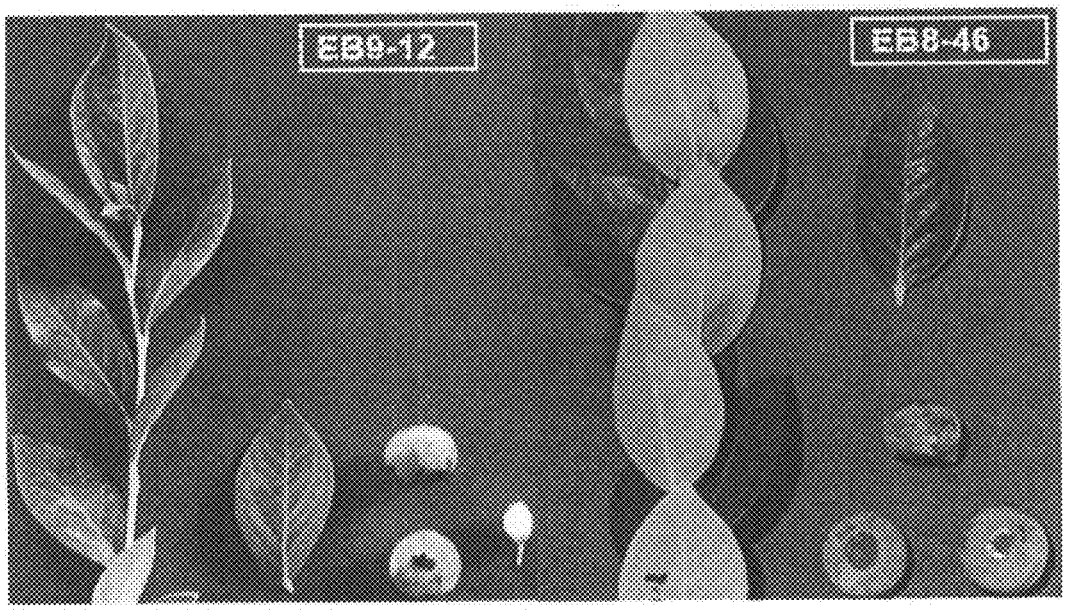
EB9-12
EB8-46